United States Patent
Gielen-Haertwig et al.

(10) Patent No.: US 7,199,136 B2
(45) Date of Patent: Apr. 3, 2007

(54) 1,4-DIHYDRO-1,4-DIPHENYLPYRIDINE DERIVATIVES

(75) Inventors: Heike Gielen-Haertwig, Monheim (DE); Volkhart Min-Jian Li, Velbert (DE); Ulrich Rosentreter, Wuppertal (DE); Karl-Heinz Schlemmer, Wuppertal (DE); Swen Allerheiligen, Essen (DE); Kevin Nash, Herts (GB); Mary Fitzgerald, Yarnton (GB)

(73) Assignee: Bayer HealthCare AG, Leverkusen (DE)

( * ) Notice: Subject to any disclaimer, the term of this patent is extended or adjusted under 35 U.S.C. 154(b) by 0 days.

(21) Appl. No.: 10/498,967

(22) PCT Filed: Dec. 9, 2002

(86) PCT No.: PCT/EP02/13931

§ 371 (c)(1),
(2), (4) Date: Mar. 28, 2005

(87) PCT Pub. No.: WO03/053930

PCT Pub. Date: Jul. 3, 2003

(65) Prior Publication Data
US 2005/0165014 A1    Jul. 28, 2005

(30) Foreign Application Priority Data

Dec. 20, 2001   (GB)  ................... 0130553.1
Jul. 17, 2002   (GB)  ................... 0216664.3

(51) Int. Cl.
C07D 401/02    (2006.01)
A61K 31/44    (2006.01)

(52) U.S. Cl. ............. 514/333; 514/355; 546/255; 546/315

(58) Field of Classification Search ........... 546/255, 546/315; 514/333, 355
See application file for complete search history.

(56) References Cited

FOREIGN PATENT DOCUMENTS

| EP | 0451654 | 10/1991 |
|----|---------|---------|
| FR | 2528425 | 12/1983 |
| WO | 9505823 | 3/1995 |

OTHER PUBLICATIONS

Hammouda et al, Journal of Heterocyclic Chemistry, vol. 23, No. 4, pp. 203-206, 1986.*

* cited by examiner

*Primary Examiner*—Zinna N. Davis

(57) ABSTRACT

The invention relates to novel 1,4-dihydro-1,4-diphenylpyridine derivatives of formula (I)

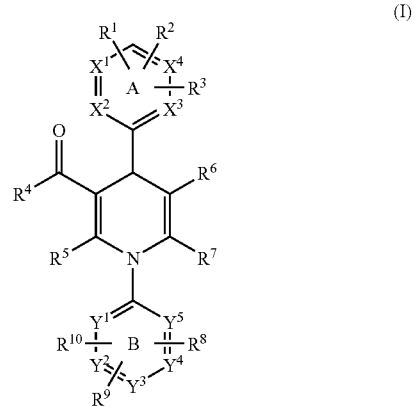

wherein the variable groups are as defined in the text and claims. Processes for their preparation, pharmaceutical compositions containing them, and methods of treatment of inflammatory processes, expecially chronic obstructive pulmonary diseases, using them are also disclosed and claimed.

15 Claims, No Drawings

1,4-DIHYDRO-1,4-DIPHENYLPYRIDINE DERIVATIVES

The present invention relates to novel 1,4-dihydro-1,4-diphenylpyridine derivatives, processes for their preparation, and their use in medicaments, especially for the treatment of chronic obstructive pulmonary diseases.

The fibrous protein elastin, which comprises an appreciable percentage of all protein content in some tissues, such as the arteries, some ligaments and the lungs, can be hydrolysed or otherwise destroyed by a select group of enzymes classified as elastases. Human leukocyte elastase (HLE, EC 3.4.21.37), also known as human neutrophil elastase (HNE), is a glycosylated, strongly basic serine protease and is found in the azurophilic granules of human polymorphonuclear leukocytes (PMN). HNE is released from activated PMN and has been implicated causally in the pathogenesis of acute and chronic inflammatory diseases. HNE is capable of degrading a wide range of matrix proteins including elastin, and in addition to these actions on connective tissue HNE has a broad range of inflammatory actions including upregulation of IL-8 gene expression, oedema formation, mucus gland hyperplasia and mucus hypersecretion. Pulmonary diseases where HNE is believed to play a role include lung fibrosis, pneumonia, acute respiratory distress syndrome (ARDS), pulmonary emphysema, including smoking-induced emphysema, chronic obstructive pulmonary diseases (COPD) and cystic fibrosis. HNE has also been causally implicated in rheumatoid arthritis, atherosclerosis, brain trauma, cancer and related conditions in which neutrophil participation is involved. Thus, inhibitors of HLE activity can be potentially useful in the treatment of a number of inflammatory diseases, especially of chronic obstructive pulmonary diseases [R. A. Stockley, *Neutrophils and protease/antiprotease imbalance*, Am. J. Respir. Crit. Care 160, S49–S52 (1999)].

Certain cationic amphiphilic 1,4-dihydropyridine derivatives useful for delivery of nucleotide containing compounds are disclosed in WO-A1-01/62946. Ethyl 6-amino-1,4-bis (4-chlorophenyl)-5-cyano-2-methyl-1,4-dihydro-3-pyridinecarboxylate has been synthesized and tested for potential antimicrobial activity as described in A. W. Erian et al., *Pharmazie* 53 (11), 748–751 (1998).

The present invention relates to compounds of the general formula (I)

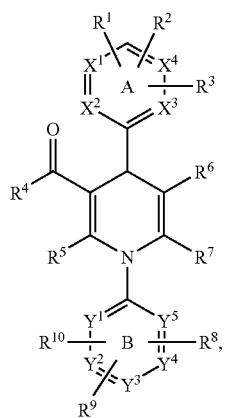

wherein
$R^1$, $R^2$, $R^3$, $R^8$, $R^9$ and $R^{10}$ independently from each other represent hydrogen, halogen, nitro, cyano, trifluoromethyl, $C_1$–$C_6$-alkyl, $C_1$–$C_6$-alkanoyl, hydroxy, $C_1$–$C_6$-alkoxy, trifluoromethoxy, amino, mono- or di-$C_1$–$C_6$-alkylamino, $C_1$–$C_6$-acylamino, $C_1$–$C_6$-alkoxycarbonylamino, carboxyl, $C_1$–$C_6$-alkoxycarbonyl or phenyl, wherein $C_1$–$C_6$-alkyl, $C_1$–$C_6$-alkanoyl, $C_1$–$C_6$-alkoxy, mono- or di-$C_1$–$C_6$-alkylamino and $C_1$–$C_6$-acylamino can be further substituted with one to three identical or different radicals selected from the group consisting of hydroxy, $C_1$–$C_4$-alkoxy, amino, mono- and di-$C_1$–$C_4$-alkylamino,
$R^4$ represents $C_1$–$C_6$-alkyl, trifluoromethyl or phenyl,
$R^5$ represents $C_1$–$C_4$-alkyl, which can be substituted with one to three identical or different radicals selected from the group consisting of hydroxy, $C_1$–$C_4$-alkoxy, amino, mono- and di-$C_1$–$C_4$-alkylamino,
$R^6$ represents cyano, aminocarbonyl, mono- and di-$C_1$–$C_4$-alkylaminocarbonyl, carboxyl or $C_1$–$C_6$-alkoxycarbonyl, wherein the alkoxy moiety can be further substituted with a radical selected from the group consisting of hydroxy, $C_1$–$C_4$-alkoxy, amino, mono- and di-$C_1$–$C_4$-alkylamino, or
$R^6$ represents a moiety of the formula

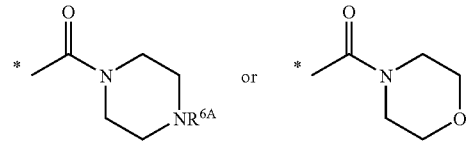

wherein $R^A$ is selected from the group consisting of hydrogen and $C_1$–$C_6$-alkyl,
$R^7$ represents hydrogen, $C_1$–$C_4$-alkyl or amino,
$X^1$, $X^2$, $X^3$ and $X^4$ independently from each other represent CH or N, wherein ring A contains either 0, 1 or 2 nitrogen atoms,
and
$Y^1$, $Y^2$, $Y^3$, $Y^4$ and $Y^5$ independently from each other represent CH or N, wherein ring B contains either 0, 1 or 2 nitrogen atoms.

In another embodiment, the present invention relates to compounds of general formula (I), wherein
$R^1$ represents hydrogen,
$R^2$, $R^3$, $R^9$ and $R^{10}$ independently from each other represent hydrogen, halogen, nitro, cyano, trifluoromethyl, $C_1$–$C_4$-alkyl, $C_1$–$C_4$-alkanoyl, hydroxy, $C_1$–$C_4$-alkoxy, trifluoromethoxy, amino, $C_1$–$C_4$-dialkylamino, $C_1$–$C_4$-acylamino, methoxycarbonylamino, tert.-butoxycarbonylamino, carboxyl, methoxycarbonyl or ethoxycarbonyl, wherein $C_1$–$C_4$-alkyl, $C_1$–$C_4$-alkanoyl, $C_1$–$C_4$-alkoxy, $C_1$–$C_4$-dialkylamino and $C_1$–$C_4$-acylamino can be further substituted with one to two identical or different radicals selected from the group consisting of hydroxy, methoxy, ethoxy, amino, dimethylamino and diethylamino,
$R^4$ represents methyl, ethyl, trifluoromethyl or phenyl,
$R^5$ represents methyl or ethyl,
$R^6$ represents cyano, aminocarbonyl, methylaminocarbonyl, dimethylaminocarbonyl, carboxyl or $C_1$–$C_4$-alkoxycarbonyl, wherein the alkoxy moiety can be further substituted with a radical selected from the group consisting of hydroxy, methoxy, ethoxy, amino, mono- and di-$C_1$–$C_4$-alkylamino, $R^7$ represents hydrogen, methyl, ethyl or amino,
$R^8$ represents hydrogen,
$X^1$, $X^2$ and $X^3$ represent CH,
$X^4$ represents CH or N,
and
$Y^1$, $Y^2$, $Y^3$, $Y^4$ and $Y^5$ represent CH.

In another embodiment, the present invention relates to compounds of general formula (I), wherein
$R^1$ and $R^2$ represent hydrogen,
$R^3$ represents fluoro, chloro, bromo, nitro, cyano, trifluoromethyl, methyl, methoxy or hydroxy,
$R^4$ represents methyl or trifluoromethyl,
$R^5$ represents methyl,
$R^6$ represents cyano, aminocarbonyl, methylaminocarbonyl, dimethylaminocarbonyl, carboxyl, methoxycarbonyl or ethoxycarbonyl,
$R^7$ represents hydrogen, methyl or amino,
$R^8$ and $R^9$ represent hydrogen,
$R^{10}$ represents fluoro, chloro, bromo, nitro, cyano, trifluoromethyl or methyl,
$X^1$, $X^2$, $X^3$ and $X^4$ represent CH,
and
$Y^1$, $Y^2$, $Y^3$, $Y^4$ and $Y^5$ represent CH.

In another embodiment, the present invention relates to compounds according to general formula (I), which have the following structure:

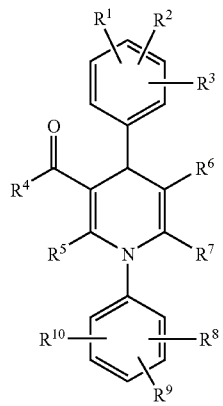

and wherein
$R^1$; $R^2$, $R^3$, $R^8$, $R^9$ and $R^{10}$ independently from each other represent hydrogen, halogen, nitro, cyano, trifluoromethyl, $C_1$–$C_6$-alkyl, $C_1$–$C_6$-alkanoyl, hydroxy, $C_1$–$C_6$-alkoxy, trifluoromethoxy, amino, mono- or di-$C_1$–$C_6$-alkylamino, $C_1$–$C_6$-acylamino, $C_1$–$C_6$-alkoxycarbonylamino, carboxyl, $C_1$–$C_6$-alkoxycarbonyl or phenyl, wherein $C_1$–$C_6$-alkyl, $C_1$–$C_6$-alkanoyl, $C_1$–$C_6$-alkoxy, mono- or di-$C_1$–$C_6$-alkylamino and $C_1$–$C_6$-acylamino can be further substituted with one to three identical or different radicals selected from the group consisting of hydroxy, $C_1$–$C_4$-alkoxy, amino, mono- and di-$C_1$–$C_4$-alkylamino,
$R^4$ represents $C_1$–$C_6$-alkyl, trifluoromethyl or phenyl,
$R^5$ represents $C_1$–$C_4$-alkyl,
$R^6$ represents cyano, carboxyl or $C_1$–$C_6$-alkoxycarbonyl, wherein the alkoxy moiety can be further substituted with a radical selected from the group consisting of hydroxy, $C_1$–$C_4$-alkoxy, amino, mono- and di-$C_1$–$C_4$-alkylamino,
and
$R^7$ represents hydrogen, $C_1$–$C_4$-alkyl or amino.

In another embodiment, the present invention relates to compounds according to general formula (I), wherein $R^3$ is cyano, which is located in para-position relative to the 1,4-dihydropyridine ring.

In another embodiment, the present invention relates to compounds according to general formula (I), wherein $R^4$ is methyl.

In another embodiment, the present invention relates to compounds according to general formula (I), wherein $R^5$ is methyl.

In another embodiment, the present invention relates to compounds according to general formula (I), wherein $R^6$ is methoxycarbonyl or ethoxycarbonyl.

In another embodiment, the present invention relates to compounds according to general formula (I), wherein $R^7$ is hydrogen, methyl or amino.

In another embodiment, the present invention relates to compounds according to general formula (I), wherein $R^{10}$ is trifluoromethyl, which is attached to $Y^2$.

The compounds according to this invention can also be present in the form of their salts, hydrates and/or solvates.

Physiologically acceptable salts are preferred in the context of the present invention.

Physiologically acceptable salts according to the invention are non-toxic salts which in general are accessible by reaction of the compounds (I) with an inorganic or organic base or acid conventionally used for this purpose. Non-limiting examples of pharmaceutically acceptable salts of compounds (I) include the alkali metal salts, e.g. lithium, potassium and sodium salts, the alkaline earth metal salts such as magnesium and calcium salts, the quaternary ammonium salts such as, for example, triethyl ammonium salts, acetates, benzene sulphonates, benzoates, dicarbonates, disulphates, ditartrates, borates, bromides, carbonates, chlorides, citrates, dihydrochlorides, fumarates, gluconates, glutamates, hexyl resorcinates, hydrobromides, hydrochlorides, hydroxynaphthoates, iodides, isothionates, lactates, laurates, malates, maleates, mandelates, mesylates, methylbromides, methylnitrates, methylsulphates, nitrates, oleates, oxalates, palmitates, pantothenates, phosphates, diphosphates, polygalacturonates, salicylates, stearates, sulphates, succinates, tartrates, tosylates, valerates, and other salts used for medicinal purposes.

Hydrates of the compounds of the invention or their salts are stoichiometric compositions of the compounds with water, such as for example hemi-, mono-, or dihydrates.

Solvates of the compounds of the invention or their salts are stoichiometric compositions of the compounds with solvents.

The present invention includes both the individual enantiomers or diastereomers and the corresponding racemates or diastereomeric mixtures of the compounds according to the invention and their respective salts. In addition, all possible tautomeric forms of the compounds described above are included according to the present invention. The diastereomeric mixtures can be separated into the individual isomers by chromatographic processes. The racemates can be resolved into the respective enantiomers either by chromatographic processes on chiral phases or by resolution.

In the context of the present invention, the substituents, if not stated otherwise, in general have the following meaning:

Alkyl in general represents a straight-chain or branched hydrocarbon radical having 1 to 6, preferably 1 to 4 carbon atoms. Non-limiting examples include methyl, ethyl, n-propyl, isopropyl, n-butyl, isobutyl, sec.-butyl, tert.-butyl, pentyl, isopentyl, hexyl, isohexyl. The same applies to radicals such as alkoxy, alkylamino, alkoxycarbonyl and alkoxycarbonylamino.

Acyl or Alkanoyl in general represents a straight-chain or branched hydrocarbon radical having 1 to 6, preferably 1 to 4 carbon atoms which has a carbonyl function at the position of attachment. Non-limiting examples include formyl, acetyl, n-propionyl, n-butyryl, isobutyryl, pivaloyl, n-hexanoyl. The same applies to radicals such as acylamino.

Alkylamino represents an alkylamino radical having one or two (independently selected) alkyl substituents, illustratively and preferably representing methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Alkylaminocarbonyl represents an alkylaminocarbonyl radical having one or two (independently selected) alkyl substituents, illustratively and preferably representing methylaminocarbonyl, ethylaminocarbonyl, n-propylaminocarbonyl, isopropylaminocarbonyl, tert-butylaminocarbonyl, n-pentylaminocarbonyl n-hexylaminocarbonyl N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-t-butyl-N-methylaminocarbonyl, N-ethyl-N-n-pentylamino-carbonyl and N-n-hexyl-N-methylaminocarbonyl.

When stated, that $X^1$, $X^2$, $X^3$ and $X^4$ as well as $Y^1$, $Y^2$, $Y^3$, $Y^4$ and $Y^5$ represent CH or N, <u>CH</u> shall also stand for a ring carbon atom, which is substituted with a substituent $R^1$, $R^2$, $R^3$ or $R^8$, $R^9$ and $R^{10}$, respectively.

A * symbol next to a bond denotes the point of attachment in the molecule.

The letters A and B are used to designate the different rings and, for the purpose of clarity, are not shown in all structures.

In another embodiment, the present invention relates to processes for synthesizing the compounds of general formula (I), characterized in that either

[A] compounds of the general formula (II)

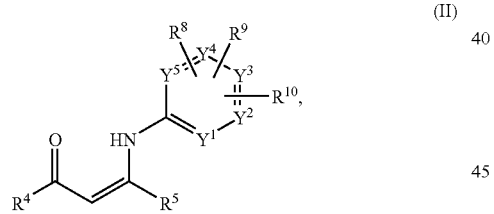

(II)

wherein $R^4$, $R^5$, $R^8$, $R^9$, $R^{10}$ and $Y^1$ to $Y^5$ have the meaning described above, are condensed in the presence of a base, in a three-component-reaction, with compounds of the general formulas (III) and (IV)

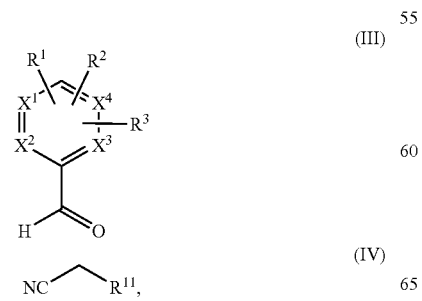

(III)

(IV)

wherein $R^1$, $R^2$, $R^3$ and $X^1$ to $X^4$ have the meaning described above, and $R^{11}$ represents cyano or $C_1$–$C_6$-alkoxycarbonyl, to give compounds of the general formula (Ia)

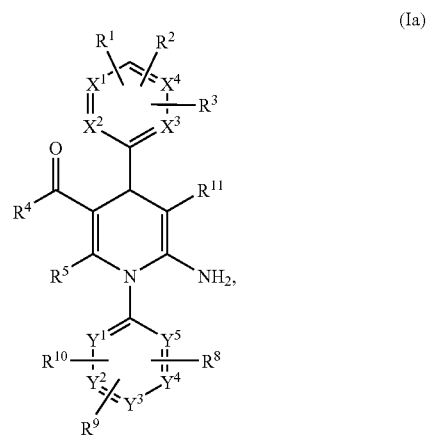

(Ia)

or

[B] compounds of the general formulas (II) and (III) are condensed in the presence of an acid, in a three-component-reaction, with compounds of the general formula (V)

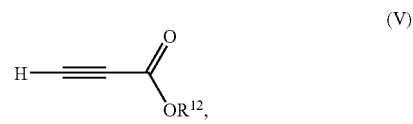

(V)

wherein $R^{12}$ represents $C_1$–$C_6$-alkyl, to give compounds of the general formula (Ib)

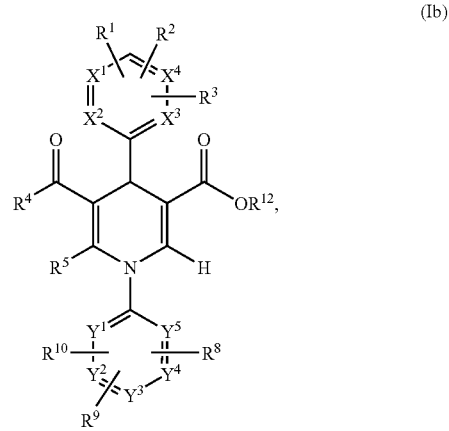

(Ib)

or

[C] compounds of the general formula (VI)

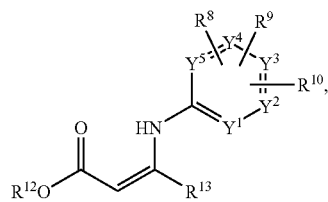 (VI)

wherein $R^8$, $R^9$, $R^{10}$, $R^{12}$ and $Y^1$ to $Y^5$ have the meaning described above,
and
$R^{13}$ represents $C_1$–$C_4$-alkyl,
are condensed in the presence of an acid or a base, in a three-component-reaction, with compounds of the general formulas (III) and (VII)

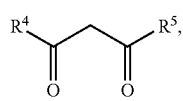 (VII)

wherein $R^4$ and $R^5$ have the meaning described above, to give compounds of the general formula (Ic)

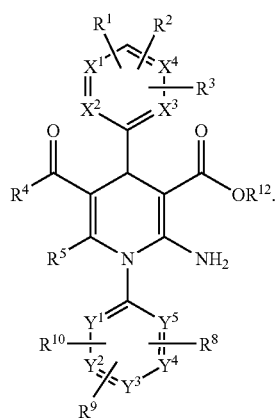 (Ic)

The processes can be illustrated by the following schemes [A] to [C]:

Scheme [A] to [C]

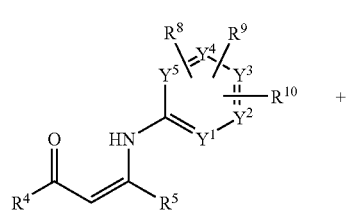 [A]

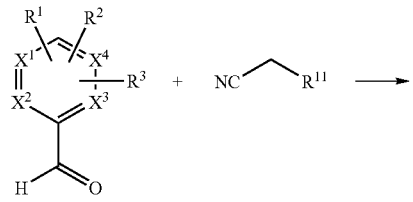

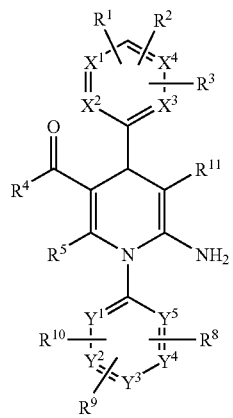

[B]

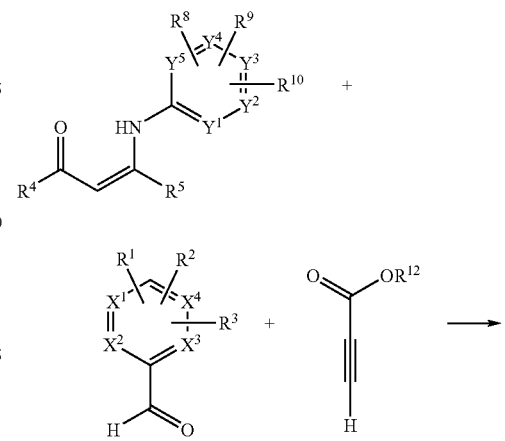

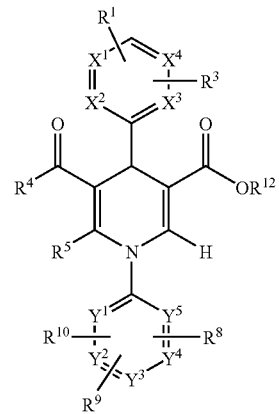

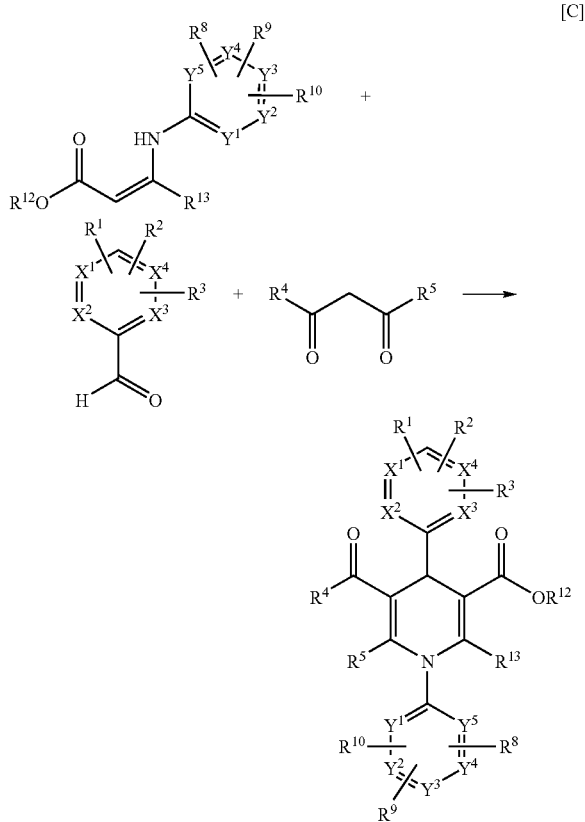

[C]

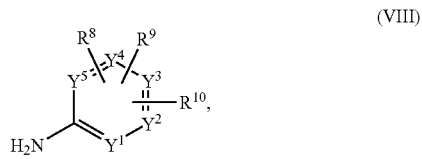

Suitable solvents for the processes [A] to [C] are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. For process [B] and [C] also acetic acid can be employed as solvent. It is also possible to use mixtures of the above-mentioned solvents. Preferred for process [A] is ethanol or a mixture of n-propanol and dimethylsulfoxide. For process [B] and [C] acetic acid or diisopropyl ether are preferred.

Suitable bases for process [A] and [C] are generally inorganic or organic bases. These preferably include cyclic amines, such as, for example, piperidine, morpholine, N-methylmorpholine, pyridine or 4-N,N-dimethylaminopyridine, or ($C_1$–$C_4$)-trialkylamines, such as, for example, triethylamine or diisopropylethylamine. Preference is given to piperidine. The base is employed in an amount from 0.1 mol to 10 mol, preferably from 1 mol to 3 mol, relative to 1 mol of the compound of the general formula (II).

Suitable acids for process [B] and [C] are generally inorganic or organic acids. These preferably include carboxylic acids, such as, for example acetic acid or trifluoroacetic acid, or sulfonic acids, such as, for example, methanesulfonic acid or p-touluenesulfonic acid. Preference for process [B] and [C] is given to acetic acid or trifluoroacetic acid. The acid is employed in an amount from 0.25 mol to 100 mol, relative to 1 mol of the compounds of the general formulas (V) and (VII), respectively.

The processes [A] to [C] are in general carried out in a temperature range from +20° C. to +150° C., preferably from +60° C. to +130° C.

The processes [A] to [C] are generally carried out at normal pressure. However, it is also possible to carry them out at elevated pressure or at reduced pressure (for example in a range from 0.5 to 5 bar).

The compounds of general formula (II) can be synthesized by reacting compounds of general formula (VII) with compounds of the general (VI)

(VIII)

$$\underset{H_2N}{\overset{R^8\ R^9}{\underset{Y^5}{\overset{Y^4}{\diagdown}}\underset{Y^1}{\overset{Y^3}{\bigg|}}\underset{Y^2}{\overset{}{=}}R^{10},}}$$

wherein $R^8$, $R^9$, $R^{10}$ and $Y^1$ to $Y^5$ have the meaning described above, in the presence of an acid, such as acetic acid or p-toluenesulfonic acid, under water-removing conditions.

The compounds of general formula (VI) can be synthesized analogously.

The compounds of the general formulas (III), (IV), (V), (VII) and (VIII) are known per se, or they can be prepared by customary methods.

Surprisingly, the compounds of the present invention show human neutrophil elastase (HNE) inhibitory activity and are therefore suitable for the preparation of medicaments for the treatment of diseases associated with HNE activity. They may thus provide an effective treatment of acute and chronic inflammatory processes, such as rheumatoid arthritis, atherosclerosis, and especially of acute and chronic pulmonary diseases, such as lung fibrosis, cystic fibrosis, pneumonia, acute respiratory distress syndrome (ARDS), in particular pulmonary emphysema, including smoking-induced emphysema, and chronic obstructive pulmonary diseases (COPD). They may also provide an effective treatment of brain trauma, cancer and other conditions in which neutrophil participation is involved.

The compounds of formula (I) according to the invention can therefore be used as active compound components for the production of medicaments. For this, they can be converted into the customary formulations such as tablets, coated tablets, aerosols, pills, granules, syrups, emulsions, suspensions and solutions in a known manner using inert, non-toxic, pharmaceutically suitable excipients or solvents. Preferably, the compounds according to the invention are used here in an amount such that their concentration in the total mixture is approximately 0.5% to approximately 90% by weight, the concentration, inter alia, being dependent on the corresponding indication of the medicament.

The above mentioned formulations are produced, for example, by extending the active compounds with solvents and/or excipients having the above properties, where, if appropriate, additionally emulsifiers or dispersants and, in the case of water as the solvent, alternatively an organic solvent, have to be added.

Administration is carried out in a customary manner, preferably orally, transdermally or parenterally, for example perlingually, buccally, intravenously, nasally, rectally or by inhalation.

For human use, in the case of oral administration, it is recommendable to administer doses of from 0.001 to 50 mg/kg, preferably of 0.01 mg/kg to 20 mg/kg. In the case of parenteral administration, such as, for example, intravenously or via mucous membranes nasally, buccally or inhalationally, it is recommendable to use doses of 0.001 mg/kg to 0.5 mg/kg.

In spite of this, if appropriate, it may be necessary to depart from the amounts mentioned above, namely depending on the body weight or the type of administration route, on the individual response towards the medicament, the manner of its formulation and the time or interval at which administration takes place. Thus, in some cases it may be sufficient to manage with less than the above mentioned minimum amount, while in other cases the upper limit mentioned must be exceeded. In the case of the administration of relatively large amounts, it may be recommendable to divide these into several individual doses over the course of the day.

A. EVALUATION OF PHYSIOLOGICAL ACTIVITY

The potential of the compounds of the invention to inhibit neutrophil elastase activity may be demonstrated, for example, using the following assays:

I. In Vitro Assays of Human Neutrophil Elastase (HNE)
Assay Contents
assay buffer: 0.1 M HEPES-NaOH buffer pH 7.4, 0.5 M NaCl, 0.1% (w/v) bovine serum albumin;
suitable concentration (see below) of HNE (18 U/mg lyophil., #20927.01, SERVA Electrophoresis GmbH, Heidelberg, Germany) in assay buffer;
suitable concentration (see below) of substrate in assay buffer;
suitable concentration of test compounds diluted with assay buffer from a 10 mM stock solution in DMSO.

EXAMPLE A

In Vitro Inhibition of HNE Using a Fluorogenic Peptide Substrate (Continuous Read-Out Signal, 384 MTP Assay Format)

In this protocol, the elastase substrate MeOSuc-Ala-Ala-Pro-Val-AMC (#324740, Calbiochem-Novabiochem Corporation, Merck KgaA, Darmstadt, Germany) is used. The test solution is prepared by mixing 10 μl of test compound dilution, 20 μl of HNE enzyme dilution (final concentration 8–0.4 μU/ml, routinely 2.1 μU/ml) and 20 μl of substrate dilution (final concentration 1 mM–1 μM, routinely 20 μM), respectively. The solution is incubated for 0–2 hrs at 37° C. (routinely one hour). The fluorescence of the liberated AMC due to the enzymatic reaction is measured at 37° C. (TECAN spectra fluor plus plate reader). The rate of increase of the fluorescence (ex. 395 nm, em. 460 nm) is proportional to elastase activity. $IC_{50}$ values are determined by RFU-versus-[I] plots. $K_m$ and $K_{m(app.)}$ values are determined by Lineweaver-Burk plots and converted to $K_i$ values by Dixon plots.

The preparation examples had $IC_{50}$ values within the range of 20 nM–20 μM in this assay. Representative data are given in table 1:

TABLE 1

| Example No. | $IC_{50}$ [nM] |
|---|---|
| 3 | 200 |
| 4 | 40 |
| 5 | 20 |
| 8 | 330 |
| 10 | 230 |

TABLE 1-continued

| Example No. | $IC_{50}$ [nM] |
|---|---|
| 12 | 180 |
| 13 | 30 |
| 14 | 20 |
| 15 | 120 |
| 17 | 9000 |
| 18 | 30 |

EXAMPLE B

In Vitro Inhibition of HNE Using a Fluorogenic, Unsoluble Elastin Substrate (Discontinuous Read-out Signal, 96 MTP Assay Format)

In this protocol the elastase substrate elastin-fluorescein (#100620, ICN Biomedicals GmbH, Eschwege, Germany) is used. The test solution is prepared by mixing 3 μl of test compound dilution, 77 μl of HNE enzyme dilution (final concentration 0.22 U/ml–2.2 mU/ml, routinely 21.7 μU/ml) and 80 μl substrate suspension (final concentration 2 mg/ml). The suspension is incubated for 0–16 hrs at 37° C. (routinely four hours) under slightly shaking conditions. To stop the enzymatic reaction, 160 μl of 0.1 M acetic acid are added to the test solution (final concentration 50 mM). The polymeric elastin-fluorescein is pulled down by centrifugation (Eppendorf 5804 centrifuge, 3.000 rpm, 10 min). The supernatant is transferred into a new MTP and the fluorescence of the liberated peptide fluorescein due to the enzymatic reaction is measured (BMG Fluostar plate reader). The rate of fluorescence (ex. 490 nm, em. 520 nm) is proportional to elastase activity. $IC_{50}$ values are determined by RFU-versus-[I] plots.

II. In Vitro PMN Elastolysis Assay

This assay is used to determine the elastolytic potential of human polymorphonuclear cells (PMNs) and assess the proportion of degradation due to neutrophil elastase [cf. Z. W. She et al., Am. J. Respir. Cell. Mol. Biol. 9, 386–392 (1993)].

Tritiated elastin, in suspension, is coated on to a 96 well plate at 10 μg per well. Test and reference [ZD-0892 (J. Med. Chem. 40, 1876–1885, 3173–3181 (1997), WO 95/21855) and α1 protease inhibitor (α1PI)] compounds are added to the wells at the appropriate concentrations. Human PMNs are separated from peripheral venous blood of healthy donors and resuspended in culture media. The neutrophils are added to the coated wells at concentrations ranging between $1 \times 10^6$ to $1 \times 10^5$ cells per well. Porcine pancreatic elastase (1.3 μM is used as a positive control for the assay, and α1PI (1.2 μM) is used as the positive inhibitor of neutrophil elastase. The cellular control is PMNs without compound at each appropriate cell density. The cells plus compounds are incubated in a humidified incubator at 37° C. for 4 hours. The plates are centrifuged to allow the harvest of cell supernatant only. The supernatant is transferred in 75 μl volumes to corresponding wells of a 96 well Lumaplate™ (solid scintillant containing plates). The plates are dried until no liquid is visible in the wells and read in a beta counter for 3 minutes per well.

Elastolysis of the $^3$H-elastin results in an increase in counts in the supernatant. An inhibition of this elastolysis shows a decrease, from the cellular control, of tritium in the supernatant. α1PI gave 83.46±3.97% (mean±s.e.m.) inhibition at 1.2 μM (n=3 different donors at $3.6 \times 10^5$ cells per well). $IC_{50}$ values are obtained for the reference compound ZD-0892 of 45.50±7.75 nM (mean±s.e.m.) (n=2 different donors at $3.6 \times 10^5$ cells per well).

Given that ZD-0892 is a selective inhibitor of PMN elastase along with the data from α1PI inhibition, these results indicate that the majority of elastin degradation by PMNs is due to the release of neutrophil elastase, and not to another elastolytic enzyme such as matrix metalloproteases (MMPs). The compounds of this invention are evaluated for their inhibitory activity in this HNE-dependent model of neutro-phil elastolysis.

III. In Vivo Model of Acute Lung Injury in the Rat

Instillation of human neutrophil elastase (HNE) into rat lung causes acute lung damage. The extent of this injury can be assessed by measuring lung haemorrhage.

Rats are anaesthetised with Hypnorm/Hypnovel/water and instilled with HNE or saline delivered by microsprayer into the lungs. Test compounds are administered by intravenous injection, by oral gavage or by inhalation at set times prior to the administration of HNE. Sixty minutes after the administration of elastase animals are killed by an anaesthetic overdose (sodium pentobarbitone) and the lungs lavaged with 2 ml heparinised phosphate buffered saline (PBS). Bronchoalveolar lavage (BAL) volume is recorded and the samples kept on ice. Each BAL sample is centrifuged at 900 r.p.m. for 10 minutes at 4–10° C. The supernatant is discarded and the cell pellet resuspended in PBS and the sample spun down again. The supernatant is again discarded and the cell pellet resuspended in 1 ml 0.1% cetyltrimethyl-anmonium bromide (CTAB)/PBS to lyse the cells. Samples are frozen until blood content is assayed. Prior to the haemorrhage assay the samples are defrosted and mixed. 100 µl of each sample are placed into a separate well of a 96 well flat-bottomed plate. All samples are tested in duplicate. 100 µl 0.1% CTAB/PBS is included as a blank. The absorbance of the well contents is measured at 415 nm using a spectrophotometer. A standard curve is constructed by measuring the OD at 415 nm of different concentrations of blood in 0.1% CTAB/PBS. Blood content values are calculated by comparison to the standard curve (included in each plate) and normalised for the volume of BAL fluid retrieved.

The compounds of this invention are evaluated intravenously, orally or by inhalation for their inhibitory activity in this model of HNE-induced haemorrhage in the rat.

B. EXAMPLES

Abbreviations:

| | |
|---|---|
| c = | concentration |
| DMSO = | dimethylsulfoxide |
| HPLC = | high performance liquid chromatography |
| LC-MS = | liquid chromatography-coupled mass spectroscopy |
| NMR = | nuclear magnetic resonance spectroscopy |
| tlc = | thin layer chromatography |

LC-MS Method:

| | |
|---|---|
| solvent A: | acetonitrile |
| solvent B: | 0.3 g 30% HCl/L water |
| column oven: | 50° C. |
| column: | Symmetry C18 2.1 × 150 mm |

| gradient: | time [min] | % A | % B | flow [ml/min] |
|---|---|---|---|---|
| | 0 | 10 | 90 | 0.9 |
| | 3 | 90 | 10 | 1.2 |
| | 6 | 90 | 10 | 1.2 |

Starting Materials:

Example 1A

4-[(3-Nitrophenyl)amino]-3-penten-2-one

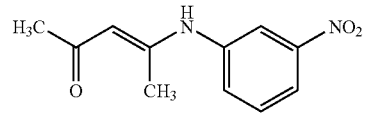

36.24 g (362 mmol) Acetylacetone, 10.00 g (72 mmol) 3-nitroaniline, and 1.25 g (7.2 mmol) 4-toluenesulfonic acid are dissolved in 100 ml toluene. The reaction mixture is refluxed overnight with a Dean-Stark trap to remove water. After cooling down to room temperature, the solvent is removed in vacuo and the residue is purified by column chromatography on silica with eluent dichloromethane.

Yield: 12.0 g (75%)

¹H-NMR (400 MHz, DMSO): δ=2.0 (s, 3H); 2.1 (s, 3H); 5.4 (s, 1H); 7.7 (m, 2H); 8.0 (m, 2H); 12.5 (s, 1H) ppm.

Example 2A

4-{[3-(Trifluoromethyl)phenyl]amino}-3-penten-2-one

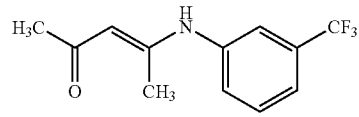

15.53 g (155 mmol) Acetylacetone, 5.00 g (31 mmol) 3-trifluoromethylaniline, and 0.53 g (3.1 mmol) 4-toluenesulfonic acid are dissolved in 50 ml toluene. The reaction mixture is refluxed overnight with a Dean-Stark trap to remove water. After cooling down to room temperature, the solvent is removed in vacuo and the residue is purified by column chromatography on silica with cyclohexane/ethylacetate mixtures as eluent.

Yield: 5.46 g (72%)

¹H-NMR (200 MHz, DMSO): δ=2.0 (s, 3H); 2.1 (s, 3H); 5.3 (s, 1H); 7.5 (m, 4H); 12.5 (s, 1H) ppm.

Example 3A

Ethyl(2E)-3-{[3-(trifluoromethyl)phenyl]amino}-2-butenoate

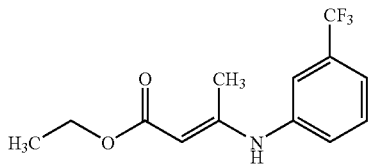

4.0 g (31 mmol) Ethyl 3-oxobutanoate, 5.0 g (31 mmol) 3-trifluoromethylaniline, and 1.86 g (31 mmol) acetic acid are dissolved in 50 ml toluene. The reaction mixture is refluxed overnight with a Dean-Stark trap to remove water. After cooling down to room temperature, the solvent is removed in vacuo and the residue is purified by column chromatography on silica with cyclohexane/ethylacetate mixtures as eluent.

Yield: 2.28 g (27%)

$^1$H-NMR (300 MHz, DMSO): δ=1.2 (t, 3H); 2.0 (s, 3H); 4.1 (q, 2H); 4.8 (s, 1H); 7.5 (m, 4H); 10.4 (s, 1H) ppm.

Example 4A

4-{[3-(Methyl)phenyl]amino}-3-penten-2-one

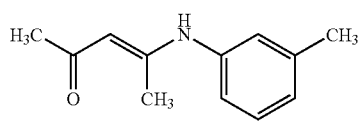

23.36 g (233 mmol) Acetylacetone, 5.00 g (47 mmol) 3-methylaniline, and 0.8 g (4.7 mmol) 4-toluenesulfonic acid are dissolved in 50 ml toluene. The reaction mixture is refluxed overnight with a Dean-Stark trap to remove water. After cooling down to room temperature, the solvent is removed in vacuo and the residue is purified by column chromatography on silica with cyclohexane/ethylacetate mixtures as eluent.

Yield: 7.7 g (87%)

$^1$H-NMR (300 MHz, DMSO): δ=2.0 (2 s, 6H); 2.3 (s, 3H); 5.2 (s, 1H); 7.0 (m, 3H); 7.2 (m, 1H) ppm.

Example 5A

4-{[3-Iodo-5-(trifluoromethyl)phenyl]amino}-3-penten-2-one

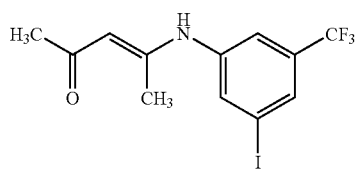

1.38 g (13.8 mmol) Acetylacetone, 3.95 g (13.8 mmol) 3-iodo-5-trifluoromethyl-aniline, and 0.1 g (1.6 mmol) 4-toluenesulfonic acid are dissolved in 150 ml toluene. The reaction mixture is refluxed for 7 h with a Dean-Stark trap to remove water. After cooling down to room temperature, the suspension is filtered. The solid is purified by recrystallisation from ethanol.

Yield: 1.8 g (34%)

$^1$H-NMR (300 MHz, DMSO): δ=2.0 (s, 3H); 2.1 (s, 3H); 5.3 (s, 1H); 7.6 (s, 1H); 7.8 (s, 1H); 7.9 (s, 1H); 12.4 (s, 1H) ppm.

Example 6A 4-({3-[(Diethylamino)methyl]phenyl}amino)-3-penten-2-one

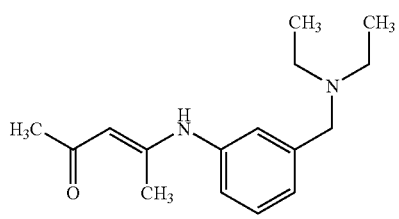

1.00 g (9.99 mmol) Acetylacetone, 1.78 g (9.99 mmol) 3-[(diethylamino)methyl]-aniline, and 0.15 g (2.5 mmol) 4-toluenesulfonic acid are dissolved in 100 ml toluene. The reaction mixture is refluxed overnight with a Dean-Stark trap to remove water. 0.05 g (0.83 mmol) 4-toluenesulfonic acid are again added and the mixture is refluxed overnight. As tlc control showed that there is some 3-[(diethylamino)-methyl]aniline left, 0.2 g (2 mmol) acetylacetone are added and refluxing is continued for 4 h. To drive the reaction to completion, 0.6 ml (9.98 mmol) acetic acid and 0.2 g (2 mmol) acetylacetone are added and the mixture is refluxed overnight with a Dean-Stark trap. After cooling down to room temperature, the solvent is removed in vacuo and the residue is purified by column chromatography on silica with dichloromethane/methanol mixtures as eluent.

Yield: 1.97 g (76%)

$^1$H-NMR (200 MHz, CDCl$_3$): δ=1.0 (t, 6H); 2.0 (s, 3H), 2.1 (s, 3H); 2.5 (q, 4H); 3.5 (s, 2H); 5.2 (s, 1H); 7.0 (m, 1H); 7.1–7.3 (m, 3M); 12.5 (s, 1H) ppm.

Example 7A

4-{[3-Methoxy-5-(trifluoromethyl)phenyl]amino}-3-penten-2-one

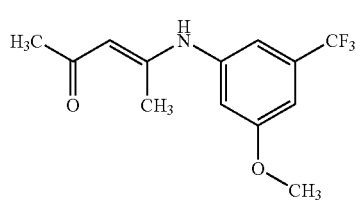

1.57 g (15.7 mmol) Acetylacetone, 3.00 g (15.7 mmol) 3-methoxy-5-(trifluoromethyl)aniline, and 0.1 g (1.6 mmol) 4-toluenesulfonic acid are dissolved in 150 ml toluene. The reaction mixture is refluxed for 7 h with a Dean-Stark trap to remove water. After cooling down to room temperature, the suspension is filtered. The solid is purified by recrystallisation from ethanol.

Yield: 2.8 g (60%)

$^1$H-NMR (300 MHz, DMSO): δ=2.0 (s, 3H); 2.1 (s, 3H); 3.8 (s, 3H); 5.3 (s, 1H); 7.1 (m, 3H); 12.4 (s, 1H) ppm.

Example 8A

4-[(3-Amino-5-tifluoromethylphenyl)amino]-3-penten-2-one

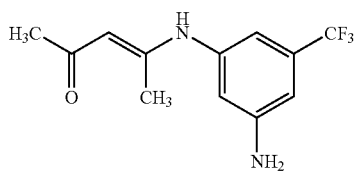

1.71 g (17.0 mmol) Acetylacetone, 3.00 g (17.0 mmol) 3-amino-5-(trifluoromethyl)-phenylamine, and 0.1 g (1.6 mmol) 4-toluenesulfonic acid are dissolved in 150 ml toluene. The reaction mixture is refluxed overnight with a Dean-Stark trap to remove water. After cooling down to room temperature, the solvent is removed in vacuo and the residue is purified by column chromatography on silica with cyclohexane/ethylacetate mixtures as eluent. The solid obtained by column chromatography is recrystallized from cyclohexane.

Yield: 0.35 g (8%)

$^1$H-NMR (200 MHz, DMSO): δ=2.0 (s, 3H); 2.1 (s, 3H); 5.2 (s, 1H); 5.7 (s, 2h); 6.5 (m, 2H); 6.6 (s, 1H); 12.4 (s, 1H) ppm.

PREPARATION EXAMPLES

Example 1

(±)-Ethyl 5-acetyl-2-amino-4-(4-bromophenyl)-6-methyl-1-(3-nitrophenyl)-1,4-di-hydro-3-pyridinecarboxylate

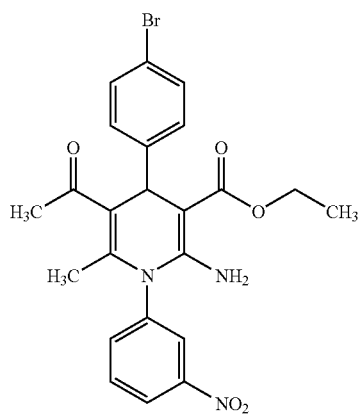

4.8 g (21.8 mmol) of Example 1A are dissolved in 30 ml ethanol, 4.0 g (21.8 mmol) 4-bromobenzaldehyde, 2.47 g (21.8 mmol) ethyl cyanoacetate, and 3.71 g (43.6 mmol) piperidine are added. The reaction mixture is stirred under reflux overnight. After cooling down to room temperature, the solvent is removed in vacuo and the residue is purified by column chromatography on silica with eluent dichloromethane.

Yield: 1.8 g (17%)

$^1$H-NMR (300 MHz, DMSO): δ=1.2 (t, 3H); 1.9 (s, 3H); 2.2 (s, 3H); 4.0 (m, 2H); 4.9 (s, 1H); 6.8 (br.s, 2H); 7.3 (m, 2H); 7.5 (m, 2H); 7.8 (m, 2H); 8.2 (m, 1H); 8.4 (m, 1H) ppm.

Example 2

(−)-Ethyl 5-acetyl-2-amino-4-(4-bromophenyl)-6-methyl-1-(3-nitrophenyl)-1,4-di-hydro-3-pyridinecarboxylate The enantiomers of Example 1 are separated by chiral HPLC [silane modified poly(N-methacryloyl-L-leucin-1-menthylamide) fixed on silica; 250×20 mm column] with iso-hexane/ethylacetate 4:1 as eluent (20 ml/min).

[α]$^{20}$=−97.6° (λ=589 nm, methanol, c=456.5 mg/100 ml)

$^1$H-NMR identical with Example 1.

Example 3

(±)-Ethyl 5-acetyl-2-amino-4-(4-bromophenyl)-6-methyl-1-[3-(trifluoromethyl)-phenyl]-1,4-dihydro-3-pyridinecarboxylate

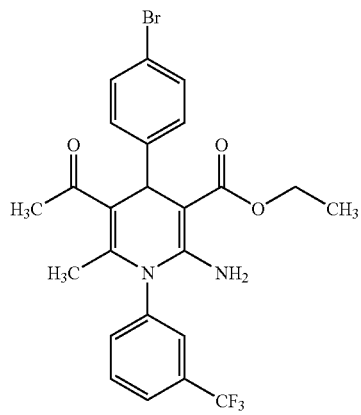

150 mg (0.62 mmol) of Example 2A are dissolved in 2 ml ethanol, 114 mg (0.62 mmol) 4-bromobenzaldehyde, 70 mg (0.62 mmol) ethyl cyanoacetate, and 105 mg (1.23 mmol) piperidine are added. The reaction mixture is stirred under reflux overnight. After cooling down to room temperature, the solvent is removed in vacuo and the residue is purified by column chromatography on silica with eluent dichloromethane.

Yield: 43 mg (13%)

$^1$H-NMR (300 MHz, DMSO): δ=1.2 (t, 3H); 1.8 (s, 3H); 2.2 (s, 3H); 4.0 (m, 2H); 4.9 (s, 1H); 6.7 (br.s, 2H); 7.3 (m, 2H); 7.5 (m, 2H); 7.7 (m, 1H); 7.8 (m, 1H); 7.8 (m, 1H); 7.9 (m, 1H) ppm.

Example 4

(±)-Ethyl 5-acetyl-2-amino-4-(4-cyanophenyl)-6-methyl-1-[3-(trifluoromethyl)-phenyl]-1,4-dihydro-3-pyridinecarboxylate

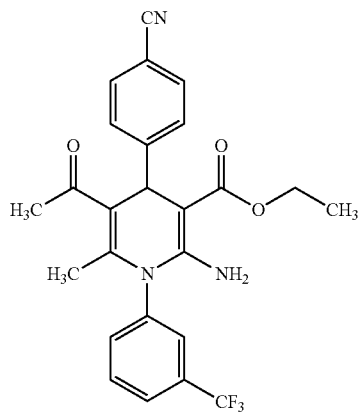

100 mg (0.41 mmol) of Example 2A are dissolved in 2 ml ethanol, 54 mg (0.41 mmol) 4-cyanobenzaldehyde, 47 mg (0.41 mmol) ethyl cyanoacetate, and 70 mg (0.82 mmol) piperidine are added. The reaction mixture is stirred under reflux overnight. After cooling down to room temperature, the solvent is removed in vacuo and the residue is purified by column chromatography on silica with eluent dichloromethane.

Yield: 26 mg (14%)

$^1$H-NMR (400 MHz, DMSO): δ=1.2 (t, 3H); 1.8 (s, 3H); 2.2 (s, 3H); 4.0 (m, 2H); 5.0 (s, 1H); 6.7 (br.s, 2H); 7.5 (m, 2H); 7.7 (m, 1H); 7.8 (m, 4H); 7.9 (m, 1H) ppm.

Example 5 and Example 6

(+) and (−)-Ethyl 5-acetyl-2-amino-4-(4-cyanophenyl)-6-methyl-1-[3-(trifluoro-methyl)phenyl]-1,4-dihydro-3-pyridinecarboxylate The enantiomers of Example 4 are separated by chiral HPLC [silane modified poly(N-methacryloyl-L-leucin-1-menthylamide) fixed on silica; 250×20 mm column] with iso-hexane/ethylacetate 4:1 as eluent (20 ml/min).

(+)-Enantiomer (Example 5):

$[α]^{20}$=+88.4° (λ=589 nm, methanol, c=453.5 mg/100 ml)

(−)-Enantiomer (Example 6):

$[α]^{20}$=−91.2° (λ=589 nm, methanol, c=471.5 mg/100 ml)

$^1$H-NMRs for Example 5 and 6 identical with Example 4.

Example 7

(±)-Ethyl 5-acetyl-4-(4-bromophenyl)-6-methyl-1-[3-(trifluoromethyl)phenyl]-1,4-dihydro-3-pyridinecarboxylate

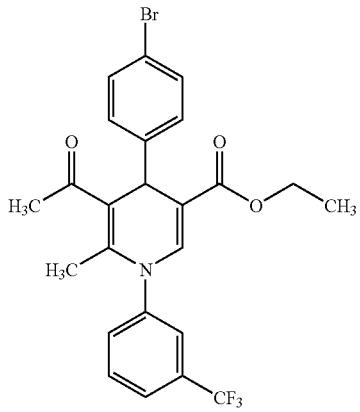

150 mg (0.62 mmol) of Example 2A are dissolved in 2 ml acetic acid, 114 mg (0.62 mmol) 4-bromobenzaldehyde, and 60 mg (0.62 mmol) ethyl propiolate are added. The reaction mixture is stirred under reflux overnight. After cooling down to room temperature, the solvent is removed in vacuo and the residue is purified by column chromatography on silica with eluent dichloromethane.

Yield: 56 mg (18%)

$^1$H-NMR (300 MHz, DMSO): δ=1.1 (t, 3H); 1.9 (s, 3H); 2.2 (s, 3H); 4.1 (m, 2H); 5.0 (s, 1H); 7.3 (m, 3H); 7.5 (m, 2H); 7.7 (m, 2H); 7.8 (m, 1H); 7.9 (s, 1H) ppm.

Example 8

(±)-Ethyl 5-acetyl-4-(4-cyanophenyl)-6-methyl-1-[3-(trifluoromethyl)phenyl]-1,4-dihydro-3-pyridinecarboxylate

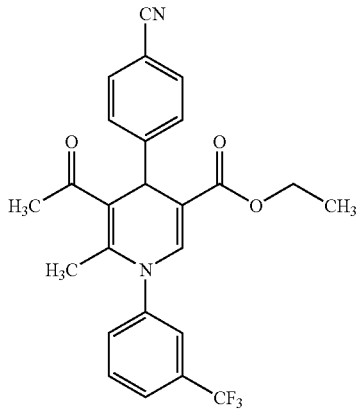

100 mg (0.41 mmol) of Example 2A are dissolved in 2 ml acetic acid, 54 mg (0.41 mmol) 4-cyanobenzaldehyde, and 40 mg (0.41 mmol) ethyl propiolate are added. The reaction mixture is stirred under reflux overnight. After cooling down to room temperature, the solvent is removed in vacuo and the residue is purified by column chromatography on silica with eluent dichloromethane.

Yield: 20 mg (11%)

¹H-NMR (300 MHz, DMSO): δ=1.1 (t, 3H); 2.0 (s, 3H); 2.2 (s, 3H); 4.1 (m, 2H); 5.1 (s, 1H); 7.3 (s, 1H); 7.6 (m, 2H); 7.8 (m, 4H); 7.8 (m, 1H); 8.0 (s, 1H) ppm.

Example 9

(±)-Ethyl 5-acetyl-4-(4-cyanophenyl)-2,6-dimethyl-1-(3-methylphenyl)-1,4-dihydro-3-pyridinecarboxylate

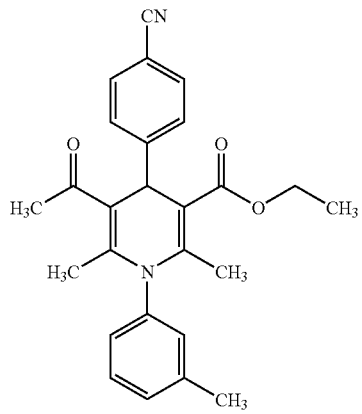

100 mg (0.46 mmol) Ethyl(2E)-3-{[3-(methyl)phenyl]amino}-2-butenoate, 75 mg. (0.57 mmol) 4-cyanobenzaldehyde, 38 mg (0.38 mmol) 2,4-pentanedione, and 87 mg (0.76 mmol) trifluoroacetic acid are dissolved in 2 ml diisopropyl ether. The reaction mixture is stirred under reflux overnight. After cooling down to room temperature, the solvent is removed in vacuo and the residue is purified by preparative HPLC.

Yield: 11 mg (7%)

¹H-NMR (300 MHz, DMSO): δ=1.2 (t, 3H); 2.0 (s, 3H); 2.0 (s, 3H); 2.2 (s, 3H); 2.4 (s, 3H); 4.1 (q, 2H); 5.1 (s, 1H); 7.0 (m, 2H); 7.3 (m, 1H); 7.4 (m, 1H); 7.5 (m, 2H); 7.8 (m, 2H) ppm.

Example 10

(±)-Ethyl 5-acetyl-4-(4-cyanophenyl)-2,6-dimethyl-1-[3-(trifluoromethyl)phenyl]-1,4-dihydro-3-pyridinecarboxylate

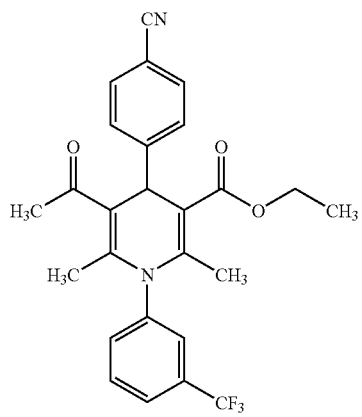

100 mg (0.37 mmol) of Example 3A, 60 mg (0.46 mmol) 4-cyanobenzaldehyde, 31 mg (0.31 mmol) 2,4-pentanedione, and 70 mg (0.61 mmol) trifluoroacetic acid are dissolved in 2 ml diisopropyl ether. The reaction mixture is stirred under reflux overnight. After cooling down to room temperature, the solvent is removed in vacuo and the residue is purified by preparative HPLC.

Yield: 7 mg (5%)

¹H-NMR (300 MHz, DMSO): δ=1.2 (t, 3H); 1.9 (s, 3H); 2.0 (s, 3H); 2.3 (s, 3H); 4.1 (q, 2H); 5.1 (s, 1H); 7.5 (m, 2M); 7.6 (m, 1H); 7.7 (m, 1H); 7.8 (m, 3H); 7.9 (m, 1H) ppm.

Example 11

Ethyl 5-acetyl-2-amino-4-(4-(trifluoromethyl)phenyl)-6-methyl-1-[3-(trifluoromethyl)phenyl]-1,4-dihydro-3-pyridinecarboxylate

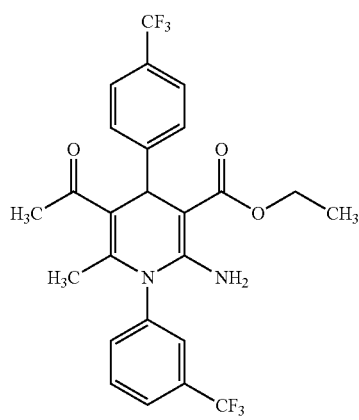

100 mg (0.41 mmol) of Example 2A are dissolved in 2 ml ethanol, 72 mg (0.41 mmol) 4-(trifluoromethyl)benzaldehyde, 47 mg (0.41 mmol) ethyl cyano-acetate, and 70 mg (0.82 mmol) piperidine are added. The reaction mixture is stirred under reflux overnight. After cooling down to room temperature, the solvent is removed in vacuo and the residue is purified by column chromatography on silica with eluent dichloromethane.

Yield: 46 mg (22%)

¹H-NMR (300 MHz, DMSO): δ=1.2 (t, 3H); 1.9 (s, 3H); 2.2 (s, 3H); 4.0 (m, 2H); 5.0 (s, 1H); 6.8 (br. s, 2H); 7.5 (m, 2H); 7.7 (m, 3H); 7.7 (m, 1H); 7.8 (m, 1H); 7.9 (m, 1H) ppm.

Example 12

Ethyl 5-acetyl-2-amino-4-(4-cyanophenyl)-6-methyl-1-[3-methylphenyl]-1,4-di-hydro-3-pyridinecarboxylate

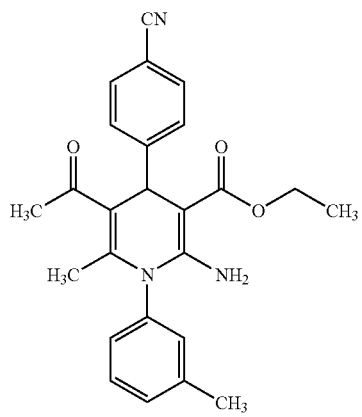

100 mg (0.53 mmol) of Example 4A are dissolved in 2 ml ethanol, 69 mg (0.53 mmol) 4-cyanobenzaldehyde, 60 mg (0.53 mmol) ethyl cyanoacetate, and 90 mg (1.06 mmol) piperidine are added. The reaction mixture is stirred under reflux overnight. After cooling down to room temperature, the solvent is removed in vacuo and the residue is purified by column chromatography on silica with eluent dichloromethane.

Yield: 21 mg (10%)

$^1$H-NMR (200 MHz, DMSO): δ=1.2 (t, 3H); 1.9 (s, 3H); 2.2 (s, 3H); 4.0 (m, 2H); 5.0 (s, 1H); 6.7 (br.s, 2H); 7.2 (m, 2H); 7.3 (m, 1H); 7.5 (m, 3H); 7.8 (m, 2H) ppm.

Example 13

5-Acetyl-2-amino-4-(4-cyanophenyl)-6-methyl-1-[3-(trifluoromethyl)phenyl]-1,4-dihydro-3-pyridinecarboxamide

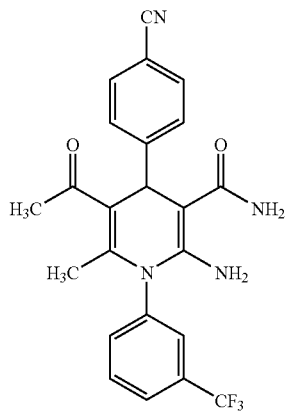

750 mg, (3.08 mmol) of Example 2A are dissolved in 5 ml ethanol, 404 mg (3.08 mmol) 4-cyanobenzaldehyde, 260 mg (3.08 mmol) cyanoacetamide, and 26 mg (0.31 mmol) piperidine are added. The reaction mixture is stirred under reflux overnight. After cooling down to room temperature, the solvent is removed in vacuo and the residue is purified by column chromatography on silica with eluent dichloromethane.

Yield: 160 mg (12%)

$^1$H-NMR (300 MHz, DMSO): δ 1.8 (s, 3H); 2.2 (s, 3H); 4.9 (s, 1H); 6.7 (br. s, 2H); 6.9 (br. s, 2H); 7.5 (m, 3H); 7.8 (m, 2H); 7.9 (m, 1H), 8.0 (m, 2H) ppm.

Example 14

5-Acetyl-4-(4-cyanophenyl)-2-imino-N,N,6-trimethyl-1-[3-(trifluoromethyl)phenyl]-1,2,3,4-tetrahydro-3-pyridinecarboxamide

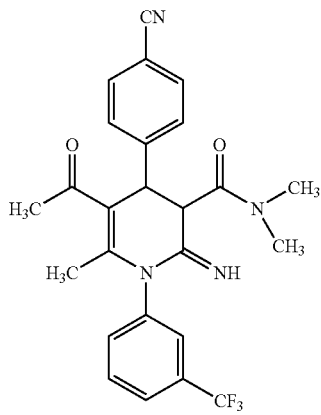

750 mg (3.08 mmol) of Example 2A are dissolved in 5 ml ethanol, 404 mg (3.08 mmol) 4-cyanobenzaldehyde, 260 mg (3.08 mmol) 2-cyano-N,N-dimethylacetamide, and 26 mg (0.31 mmol) piperidine are added. The reaction mixture is stirred under reflux overnight. After cooling down to room temperature, the solvent is removed in vacuo and the residue is purified by column chromatography on silica with eluent dichloromethane.

Yield: 88 mg (6%)

$^1$H-NMR (300 MHz, DMSO): δ=2.0 (s, 3H); 2.1 (s, 3H), 2.5 (s, 3H); 2.9 (s, 3H); 4.1 (d, 1H); 4.5 (d, 1H); 7.6 (m, 3H); 7.7 (m, 1H); 7.8 (m, 3H); 8.2 (s, 1H) ppm.

Example 15

5-Acetyl-2-amino-4-(4-cyanophenyl)-6-methyl-1-[3-(trifluoromethyl)phenyl]-1,4-dihydro-3-pyridinecarbonitrile

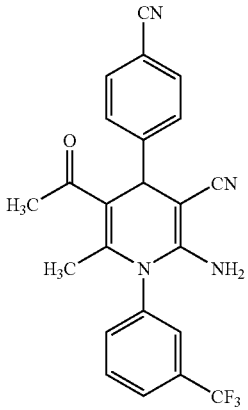

750 mg (3.08 mmol) of Example 2A are dissolved in 5 ml ethanol, 404 mg (3.08 mmol) 4-cyanobenzaldehyde, 204 mg (3.08 mmol) malononitrile, and 26 mg (0.31 mmol) piperidine are added. The reaction mixture is stirred under reflux overnight. After cooling down to room temperature, the solvent is removed in vacuo and the residue is purified by column chromatography on silica with eluent cylclohexane/ethyl acetate.

Yield: 43 mg (3%)

LC-MS: retention time 3.17 min., m/z=423 [M+H]+.

Example 16

Ethyl 5-acetyl-2-amino-4-(4-cyanophenyl)-1-[3-iodo-5-(trifluoromethyl)phenyl]-6-methyl-1,4-dihydro-3-pyridinecarboxylate

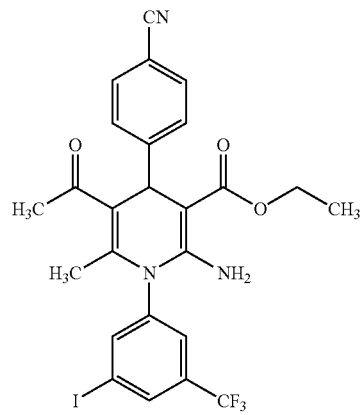

200 mg (0.54 mmol) of Example 5A are dissolved in 2.5 ml ethanol, 71.1 mg (0.54 mmol) 4-cyanobenzaldehyde, 61.3 mg (0.54 mmol) ethyl cyanoacetate, and 4.6 mg (0.05 mmol) piperidine are added. The reaction mixture is stirred under reflux for 30 h. After cooling down to room temperature, the solvent is removed in vacuo and the residue is purified by column chromatography on silica with eluent cylclohexane/ethyl acetate. The solid obtained by column chromatography is dissolved in ethanol. Water is added until a solid precipitates. The suspension is filtered and the solvent of the filtrate is removed in vacuo.

Yield: 18 mg (5%)

1H-NMR (300 MHz, DMSO): δ=1.1 (t, 3H); 1.8 (s, 3H); 2.2 (s, 3H); 4.0 (q, 2H); 4.9 (s, 1H); 6.9 (s, 2H); 7.5 (d, 2H); 7.7 (d, 2H); 7.8 (s, 1H); 8.1 (s, 1H); 8.2 (s, 1H) ppm.

Example 17

Ethyl 5-acetyl-2-amino-4-(4-cyanophenyl)-1-{3-[(diethylamino)methyl]phenyl}-6-methyl-1,4-dihydro-3-pyridinecarboxylate

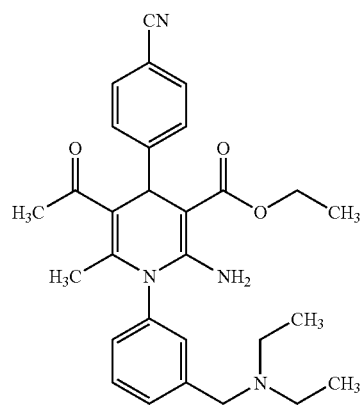

500 mg (1.92 mmol) of Example 6A are dissolved in 3.0 ml ethanol, 265 mg (1.92 mmol) 4-cyanobenzaldehyde, 217 mg (1.92 mmol) ethyl cyanoacetate, and 49 mg (0.58 mmol) piperidine are added. The reaction mixture is stirred under reflux for 48 h. 115 mg (1.34 mmol) piperidine are added and the mixture is stirred under reflux for another 6 h. After cooling down to room temperature, the solvent is removed in vacuo and the residue is purified by preparative HPLC with eluent acetonitrile/water.

Yield: 57 mg (5%)

1H-NMR (200 MHz, DMSO): δ=1.0 (t, 6H); 1.2 (t, 3H); 1.9 (s, 3H); 2.2 (s, 3H); 2.5 (m, 4H); 3.6 (s, 2H); 4.0 (q, 2H); 5.0 (s, 1); 6.7 (br. s, 2H); 7.2 (, 2H); 7.5 (m, 4H); 7.8 (d, 2H) ppm.

Example 18

Ethyl 5-acetyl-2-amino-4-(4-cyanophenyl)-1-[3-methoxy-5-(trifluoromethyl)phenyl]-6-methyl-1,4-dihydro-3-pyridinecarboxylate

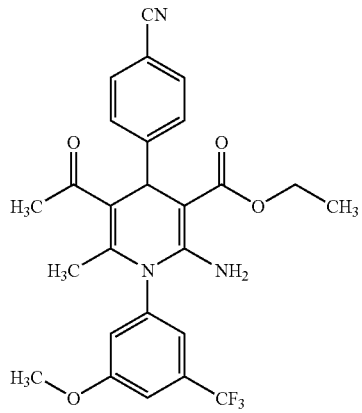

200 mg (0.73 mmol) of Example 7A are dissolved in 2.5 ml ethanol, 95.9 mg (0.73 mmol) 4-cyanobenzaldehyde, 82.8 mg (0.73 mmol) ethyl cyanoacetate, and 6.2 mg (0.07 mmol) piperidine are added. The reaction mixture is stirred under reflux overnight. After cooling down to room temperature, the solvent is removed in vacuo and the residue is purified by preparative BPLC with eluent acetonitrile/water.

Yield: 59 mg (15%)

1H-NMR (300 MHz, DMSO): δ=1.2 (t, 3H); 1.9 (s, 3H); 2.2 (s, 3H); 3.9 (s, 3H); 4.0 (q, 2H); 5.0 (s, 1H); 6.8 (br. s, 2H); 7.3 (m, 2H); 7.4 (s, 1H); 7.5 (d, 2H); 7.8 (d, 2H) ppm.

Example 19

Ethyl 5-acetyl-2-amino-1-[3-amino-5-(trifluoromethyl)phenyl]-4-(4-cyanophenyl)-6-methyl-1,4-dihydro-3-pyridinecarboxylate

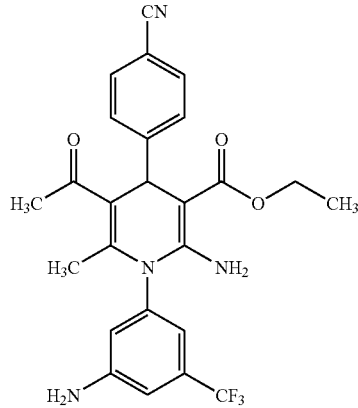

200 mg (0.77 mmol) of Example 8A are dissolved in 2.5 ml ethanol; 107 mg (0.77 mmol) 4-cyanobenzaldehyde, 87.6 mg (0.77 mmol) ethyl cyanoacetate, and 20 mg (0.23 mmol) piperidine are added. The reaction mixture is stirred under reflux overnight. After cooling down to room temperature, the solvent is removed in vacuo and the residue is purified by preparative HPLC with eluent acetonitrile/water.

Yield: 50.5 mg (12%)

$^1$H-NMR (300 MHz, DMSO): δ=1.2 (t, 3H); 2.0 (s, 3H); 2.3 (s, 3H); 4.1 (q, 2H); 5.0 (s, 1H); 6.0 (s, 2H); 6.7 (s, 2H); 6.8 (s, 2H); 7.1 (s, 1H); 7.4 (d, 2H); 7.7 (d, 2H) ppm.

Example 20

Ethyl 5'-acetyl-2'-amino-6'-methyl-1'-[3-(trifluoromethyl)phenyl]-1',4'-dihydro-3,4'-bipyridine-3'-carboxylate

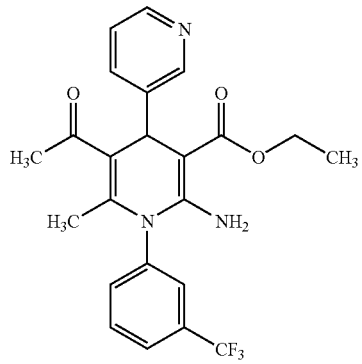

100 mg (0.41=mol) of Example 2A are dissolved in 5 ml ethanol, 44 mg (0.41 mmol) nicotinaldehyde, 47 mg (0.41 mmol) ethyl cyanoacetate, and 70 mg (0.82 mmol) piperidine are added. The reaction mixture is stirred under reflux overnight. After cooling down to room temperature, the solvent is removed in vacuo and the residue is purified by column chromatography on silica with eluent dichloromethane.

Yield: 19 mg (10%)

$^1$H-NMR (300 MHz, DMSO): δ=2.0 (s, 3H); 1.8 (s, 3H); 2.2 (s, 3H); 4.0 (m, 2H); 4.9 (s, 1H); 6.7 (m, 2H); 7.3 (m, 1H); 7.7 (m, 2H); 7.8 (m, 2H); 7.9 (m, 1H); 8.4 (m, 1H); 8.5 (m, 1H) ppm.

C. OPERATIVE EXAMPLES RELATING TO PHARMACEUTICAL COMPOSITIONS

The compounds according to the invention can be converted into pharmaceutical preparations as follows:

Tablet:

Composition:

100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Orally Administrable Suspension:

Composition:

1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 ml of oral suspension.

Preparation:

The Rhodigel is suspended in ethanol and the active component is added to the suspension. The water is added with stirring. Stirring is continued for about 6 h until the swelling of the Rhodigel is complete.

The invention claimed is:

1. A compound of the formula (I)

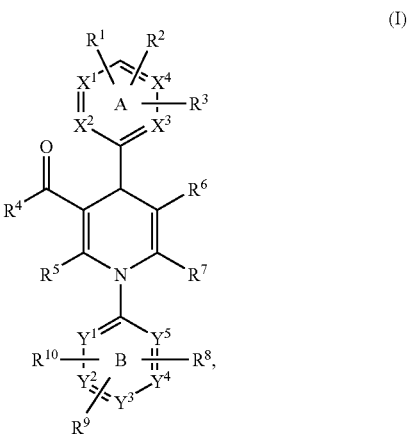

wherein $R^1$, $R^2$, $R^3$, $R^8$, $R^9$ and $R^{10}$ independently from each other represent hydrogen, halogen, nitro, cyano, trifluoromethyl, $C_1$–$C_6$-alkyl, $C_1$–$C_6$-alkanoyl, hydroxy, $C_1$–$C_6$-alkoxy, trifluoromethoxy, amino, mono- or di-$C_1$–$C_6$-alkylamino, $C_1$–$C_6$-acylamino, $C_1$–$C_6$-alkoxycarbonylamino, carboxyl, $C_1$–$C_6$-alkoxycarbonyl or phenyl, wherein $C_1$–$C_6$-alkyl, $C_1$–$C_6$-alkanoyl, $C_1$–$C_6$-alkoxy, mono- or di-$C_1$–$C_6$-alkylamino and $C_1$–$C_6$-acylamino can be further substituted with one to three identical or different radicals selected from the group consisting of hydroxy, $C_1$–$C_4$-alkoxy, amino, and mono- and di-$C_1$–$C_4$-alkylamino, $R^4$ represents $C_1$–$C_6$-alkyl, trifluoromethyl or phenyl, $R^5$ represents $C_1$–$C_4$-alkyl, which can be substituted with one to three identical or different radicals selected from the group consisting of hydroxy, $C_1$–$C_4$-alkoxy, amino, and mono- and di-$C_1$–$C_4$-alkylamino, $R^6$ represents cyano, aminocarbonyl, mono- and di-$C_1$–$C_4$-alkylaminocarbonyl, carboxyl or $C_1$–$C_6$-alkoxycarbonyl, wherein the alkoxy moiety can be further substituted with a radical selected from the group consisting of hydroxy, $C_1$–$C_4$-alkoxy, amino, and mono- and di-$C_1$–$C_4$-alkylamino, or $R^6$ represents a moiety of the formula

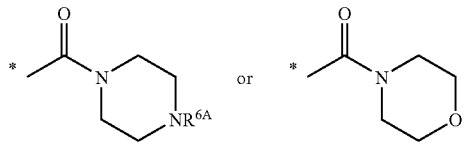

wherein $R^4$ is selected from the group consisting of hydrogen and $C_1$–$C_6$-alkyl, $R^7$ represents hydrogen, $C_1$–$C_4$-alkyl or amino, $X^1$, $X^2$, $X^3$ and $X^4$ independently from each other represent CH or N, wherein ring A contains either 0, 1 or 2 nitrogen atoms, and $Y^1$, $Y^2$, $Y^3$, $Y^4$ and $Y^5$ independently from each other represent CH or N, wherein ring B contains either 0, 1 or 2 nitrogen atoms or a salt, hydrate, or solvate thereof.

2. The compounds of formula (I) according to claim 1, wherein $R^1$ represents hydrogen, $R^2$, $R^3$, $R^9$ and $R^{10}$ independently from each other represent hydrogen, halogen, nitro, cyano, trifluoromethyl, $C_1$–$C_4$-alkyl, $C_1$–$C_4$-alkanoyl, hydroxy, $C_1$–$C_4$-alkoxy, trifluoromethoxy, amino, $C_1$–$C_4$-dialkylamino, $C_1$–$C_4$-acylamino, methoxy-carbonylamino, tert.-butoxycarbonylamino, carboxyl, methoxycarbonyl or ethoxycarbonyl, wherein $C_1$–$C_4$-alkyl, $C_1$–$C_4$-alkanoyl, $C_1$–$C_4$-alkoxy, $C_1$–$C_4$-dialkylamino and $C_1$–$C_4$-acylamino can be further substituted with one to two identical or different radicals selected from the group consisting of hydroxy, methoxy, ethoxy, amino, dimethylamino and diethylamino, $R^4$ represents methyl, ethyl, trifluoromethyl or phenyl, $R^5$ represents methyl or ethyl, $R^6$ represents cyano, aminocarbonyl, methylaminocarbonyl, dimethylaminocarbonyl, carboxyl or $C_1$–$C_4$-alkoxycarbonyl, wherein the alkoxy moiety can be further substituted with a radical selected from the group consisting of hydroxy, methoxy, ethoxy, amino, and mono- and di-$C_1$–$C_4$-alkylamino, $R^7$ represents hydrogen, methyl, ethyl or amino, $R^8$ represents hydrogen, $X^1$, $X^2$ and $Y^3$ represent CH, $X^4$ represents CH or N, and $Y^1$, $Y^2$, $Y^3$, $Y^4$ and $Y^5$ represent CH.

3. The compounds of formula (I) according to claim 1, wherein $R^1$ and $R^2$ represent hydrogen, $R^3$ represents fluoro, chloro, bromo, nitro, cyano, trifluoromethyl, methyl, methoxy or hydroxy, $R^4$ represents methyl or trifluoromethyl, $R^5$ represents methyl, $R^6$ represents cyano, aminocarbonyl, methylaminocarbonyl, dimethylaminocarbonyl, carboxyl, methoxycarbonyl or ethoxycarbonyl, $R^7$ represents hydrogen, methyl or amino, $R^8$ and $R^9$ represent hydrogen, $R^{10}$ represents fluoro, chloro, bromo, nitro, cyano, trifluoromethyl or methyl, $X^1$, $X^2$, $X^3$ and $X^4$ represent CH, and $Y^1$, $Y^2$, $Y^3$, $Y^4$ and $Y^5$ represent CH.

4. The compounds of formula (I) according to claim 1, wherein $R^3$ is cyano, which is located in para-position relative to the 1,4-dihydropyridine ring.

5. The compound of formula (I) according to claim 1, wherein $R^4$ is methyl.

6. The compound of formula (I) according to claim 1, wherein $R^5$ is methyl.

7. The compound of formula (I) according to claim 1, wherein $R^6$ is methoxycarbonyl or ethoxycarbonyl.

8. The compound of formula (I) according to claim 1, wherein $R^7$ is hydrogen, methyl or amino.

9. The compound of formula (I) according to claim 1, wherein $R^{10}$ is trifluoromethyl, which is attached to $Y^2$.

10. A processes for synthesizing the compounds of formula (I) as defined in claims 1 to 9, wherein either

[A] a compound of the formula (II)

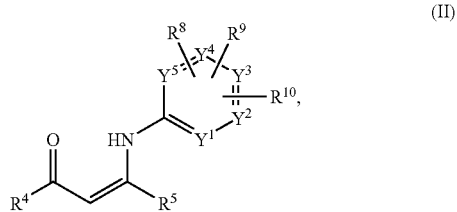

wherein $R^4$, $R^5$, $R^8$, $R^9$, $R^{10}$ and $Y^1$ to $Y^5$ have the meanings described in claim 1, is condensed in the presence of a base with compounds of the formulas (III) and (IV)

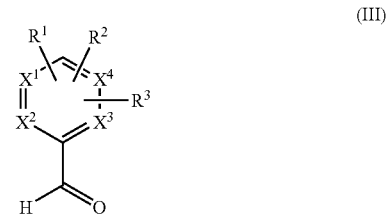

wherein $R^1$, $R^2$, $R^3$ and $X^1$ to $X^4$ have the meanings described in claim 1, and $R^{11}$ represents cyano or $C_1$–$C_6$-alkoxycarbonyl, to give a compound of the formula (Ia)

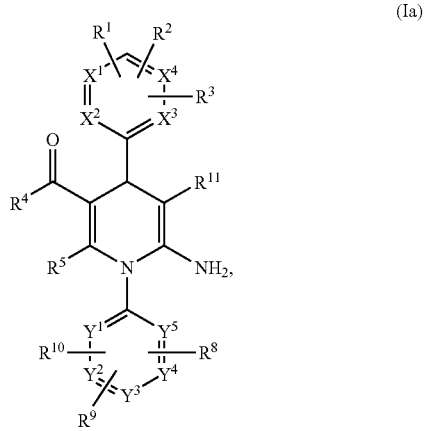

or

[B] compounds of the formulas (II) and (III) are condensed in the presence of an acid with a compound of the formula (V)

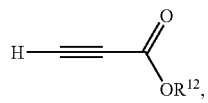
(V)

wherein $R^{12}$ represents $C_1-C_6$-alkyl,
to give a compound of the formula (Ib)

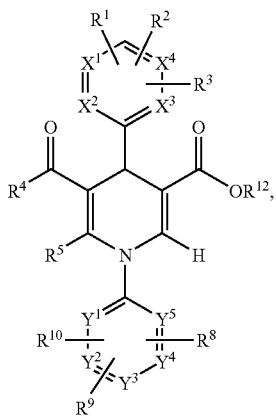
(Ib)

or

[C] a compound of the general formula (VI)

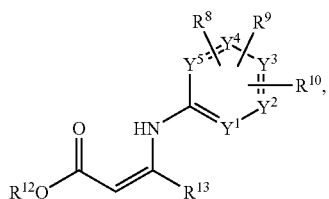
(VI)

wherein $R^8$, $R^9$, $R^{10}$, $R^{12}$ and $Y^1$ to $Y^5$ have the meanings described in claim 1, and
$R^{13}$ represents $C_1-C_4$-alkyl,
is condensed in the presence of an acid or a base with compounds of the formulas (III) and (VII)

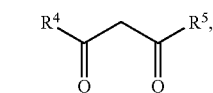
(VII)

wherein $R^4$ and $R^5$ have the meanings described in claim 1,
to give a compound of the formula (Ic)

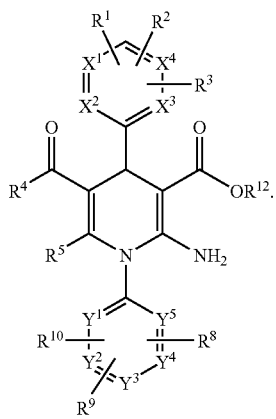
(Ic)

11. A pharmaceutical composition comprising at least one compound of general formula (I) as defined in claims 1 to 9 and a pharmacologically acceptable diluent.

12. A process for the preparation of the composition of claim 11 comprising bringing one or more compounds of formula (I) as defined in claims 1 to 9 together with customary auxiliaries into a suitable application form.

13. A method for the treatment of acute and chronic inflammatory processes comprising administering an effective amount of a compound of formula (I) as defined in claim 1.

14. The method of claim 13, wherein the inflammatory process is chronic obstructive pulmonary disease.

15. A method for controlling chronic obstructive pulmonary disease in humans and animals comprising administration of an neutrophil elastase inhibitory amount of at least one compound according to any of claims 1 to 9.

* * * * *